US005570696A

United States Patent [19]
Arnold et al.

[11] Patent Number: 5,570,696
[45] Date of Patent: Nov. 5, 1996

[54] METHOD AND APPARATUS FOR ASSESSING MYOCARDIAL ELECTRICAL STABILITY

[75] Inventors: Jeffrey M. Arnold, Wellesley; Paul Albrecht, Bedford; Kevin S. Librett, Boston; Richard J. Cohen, Waban, all of Mass.

[73] Assignee: Cambridge Heart, Inc., Bedford, Mass.

[21] Appl. No.: 187,275

[22] Filed: Jan. 26, 1994

[51] Int. Cl.$^6$ .................................................. A61B 5/0452
[52] U.S. Cl. .......................................... 128/707; 128/704
[58] Field of Search .................................. 128/702–705, 128/707, 696; 364/413.06

[56] References Cited

U.S. PATENT DOCUMENTS

| | | | |
|---|---|---|---|
| 4,732,157 | 3/1988 | Kaplan et al. | 128/702 |
| 4,802,491 | 2/1989 | Cohen et al. | 128/702 |
| 5,010,888 | 4/1991 | Jadvar et al. | 128/696 |
| 5,148,812 | 9/1992 | Verrier et al. | 128/704 |
| 5,234,404 | 8/1993 | Tuttle et al. | 128/898 X |
| 5,265,617 | 11/1993 | Verrier et al. | 128/704 |
| 5,323,783 | 6/1994 | Henkin et al. | 128/703 |

OTHER PUBLICATIONS

D. R. Adam et al., "Fluctuations in T–Wave Morphology and Susceptibility of Ventricular Fibrillation", Journal of Electrocardiology, 17(3), 1984, 209–218.

D. R. Adam et al., "Estimation of Ventricular Vulnerability of Fibrillation Through T–Wave Time Series Analysis", Computers in Cardiology, 307–310, 1981.

D. R. Adam et al., "Ventricular Fibrillations and Fluctuations in the Magnitude of the Repolarization Vector", Computers in Cardiology, 241–244, 1982.

A. L. Ritzenberg et al., "Period multupling–evidence for nonlinear behavior of the canine heart", Nature, 307, 159–161, 1984.

J. M. Smith et al., "Subtle Alternating Electrocardiographic Morphology as an Indicator of Decreased Cardiac Electrical Stability", Computers in Cardiology, 109–113, 1985.

J. M. Smith et al., "Electrical Alternans and Cardiac Electrical Instability", Circulation, 77, 110–121, 1988.

Rosenbaum et al., "Electrical Alternans and Vulnerability to Ventricular Arrhythmias", The New England Journal of Medicine, vol. 330, No. 4, pp. 235–1011, Jan. 27, 1994.

Verrier et al., "Electrophysiologic Basis for T Wave Alternans as an Index of Vulnerability to Ventricular Fibrillation", Journal of Cardiovascular Electrophysiology, vol. 5, No. 5, May 1994.

Michael E. Ring et al., "Exercise–induced ST Segment Alternans", American Heart Journal, vol. 111, No. 5, May 1986.

B. D. Nearing et al., "Dynamic Tracking of Cardiac Vulnerability by Complex Demodulation of the T Wave", Verrier, Science, 252, 437–440.

B. D. Nearing et al., "Personal Computer System for Tracking Cardiac Vulnerability by Complex Demodulation of the T Wave", Journal of Applied Physiology, 74, 2606–2612, 1993.

Primary Examiner—William E. Kamm
Assistant Examiner—Jeffrey R. Jastrzab
Attorney, Agent, or Firm—Choate, Hall & Stewart

[57] ABSTRACT

The temporal pattern of cycle-to-cycle variability in physiologic waveforms, such as alternans, is assessed by applying transducers to a subject, recording physiologic signals, and analyzing the cycle-to-cycle variation in waveform morphology. Preferred embodiments include the application of physiologic stress to the subject in order to adjust heart rate to the desired range, real-time analysis of waveform variability, reduction in the effect of intercycle variability on waveform variability, improved techniques for determining the statistical significance of the amplitude of a temporal pattern of variability, handling of abnormal beats such as atrial and ventricular premature beats, and assessment of the statistical significance of a measured level of a temporal pattern of variability.

60 Claims, 2 Drawing Sheets

METHOD AND APPARATUS FOR ASSESSING MYOCARDIAL ELECTRICAL STABILITY

BACKGROUND OF THE INVENTION

This invention relates to method and apparatus for assessing the electrical stability of the heart, and more particularly to the measurement of alternation of the morphology of electrocardiographic complexes which has a strong correlation with myocardial electrical stability.

Disturbances of electrical conduction processes in the heart are a major cause of morbidity and mortality. Sudden cardiac death, resulting from disturbances of electrical conduction in the heart, results in approximately 400,000 fatalities per year in the United States alone. The mechanism responsible for the great majority of sudden cardiac deaths is ventricular fibrillation, a disorganized pattern of electrical activity in the ventricles of the heart which leads to a disorganized pattern of mechanical contraction in the heart resulting in the cessation of effective pumping action and thus death. In addition, another disturbance of heart conduction processes, ventricular tachycardia, reduces the effectiveness of the pumping action of the heart. Ventricular tachycardia can thus cause loss of consciousness(syncope) or death. Even in cases where ventricular fibrillation itself does not cause death, ventricular tachycardia can degenerate into ventricular fibrillation which is lethal.

Effective means are now available to treat patients with electrical instabilities of the heart. For example, the internal programmed cardioverter/defibrillator is effective in preventing sudden cardiac death. This implanted device can terminate ventricular tachycardia and fibrillation by delivering an electric shock to the heart. Also antiarrhythmic drugs are available which modify the electrical properties of the heart. These drugs when used appropriately may render the heart electrically more stable; however, these drugs under other circumstances can also cause the heart to become more susceptible to ventricular tachycardia and fibrillation.

The first step in preventing sudden cardiac death is identifying individuals at risk. Currently, the procedure felt to be the most effective in identification of risk is invasive electrophysiologic testing. In this procedure catheter electrodes are advanced into the heart and by delivering electrical impulses to the heart a deliberate attempt is made to initiate ventricular tachycardia. This invasive procedure is only suitable for stratifying risk in individuals already known to be at high risk; commonly this procedure is used in individuals who have been successfully resuscitated from an episode of sudden cardiac death. This invasive procedure is also used to evaluate the effectiveness of antiarrhythmic drugs.

Clearly invasive electrophysiologic testing is not suitable for screening large populations of individuals for risk of serious ventricular arrhythmias. A variety of non-invasive measures have been used to stratify risk including measurement of the ejection fraction of the heart, measurement of the signal average electrocardiogram, measurement of heart rate variability, and measurement of ambient ventricular ectopic activity on a 24 hour electrocardiogram. These methods generally are not sufficiently predictive of risk to justify invasive testing or treatment of an asymptomatic individual.

Recently, a powerful non-invasive technique for assessing susceptibility to ventricular arrhythmias has been developed ("Method and Apparatus for Assessing Myocardial Electrical Stability" by R. J. Cohen and J. M. Smith, U.S. Pat. No. 4,802,491, February 1989; "Method and Apparatus for Quantifying Beat-to-Beat Variability in Physiologic Waveforms" by D. T. Kaplan and R. J. Cohen, U.S. Pat. No. 4,732,157, March 1988, "Fluctuations in T-Wave Morphology and Susceptibility to Ventricular Fibrillation" by D. R. Adam et. al., Journal of Electrocardiology, 17(3), 1984, 209–218; "Estimation of Ventricular Vulnerability to Fibrillation Through T-Wave Time Series Analysis" by D. R. Adam, S. Akselrod and R. J. Cohen, Computers in Cardiology 1981, 307–310; "Ventricular Fibrillation and Fluctuations in the Magnitude of the Repolarization Vector" by D. R. Adam et. al., Computers in Cardiology 1982, 241–244; "Period multupling-evidence for nonlinear behavior of the canine heart" by A. L. Ritzenberg, D. R. Adam and R. J. Cohen, Nature, 307, 1984, 159–161; "Subtle Alternating Electrocardiographic Morphology as an Indicator of Decreased Cardiac Electrical Stability" by J. M. Smith et. al., Computers in Cardiology 1985, 109–113; "Electrical alternans and cardiac electrical instability" by J. M. Smith et. al., Circulation, 77, 1988, 110–121; "The stochastic nature of cardiac electrical instability theory and experiment" by J. M. Smith, doctoral thesis, Massachusetts Institute of Technology, 1986; "Dynamic Tracking of Cardiac Vulnerability by Complex Demodulation of the T Wave" by B. D. Nearing, A. H. Huang and R. L. Verrier, Science, 252, 437–440; "Personal computer system for tracking cardiac vulnerability by complex demodulation of the T wave" by B. D. Nearing and R. L. Verrier, Journal of Applied Physiology, 74, 1993, 2606–2612). This technology involves quantifying a temporal pattern of subtle cycle-to-cycle variability in physiologic waveforms to assess physiologic stability, in particular this technology involves quantifying the temporal pattern of beat-to-beat variability in the electrocardiographic waveform to obtain a measure of the electrical stability of the heart. This variability is usually too small to be detected by visual inspection of the electrocardiogram and involves stochastic variability in waveform morphology from one cycle to another. In particular, a temporal pattern of variability of 'alternans' is measured which corresponds to a variation in electrocardiographic waveforms on an every other beat basis, an ABABAB pattern of variability in waveform morphology. In order to make analysis of cycle-to-cycle variability in physiologic waveforms a practical clinical tool for the assessment of physiologic stability a number of improvements not taught in any of the references above are required.

One of the most significant limitations in the prior art regarding the use of physiologic waveform variability to assess myocardial electrical stability is the use of invasive electrical pacing of the heart. For example, in the human studies reported in Smith et. al. [1988, cited above] the heart was electrically paced by means of endocardial catheters to achieve a heart rate of between 100 and 150 beats per minute. Placing of these catheters into the heart is a highly invasive, risky, and expensive procedure and thus greatly limits the widespread applicability of this method to evaluating the risk of sudden death in patients.

Pacing the heart by means of catheters placed in the heart largely eliminates variability in the interbeat interval which is believed to interfere with development of electrical alternans. Previous attempts to measure electrical alternans in resting subjects not being paced, did not provide results which were predictive of susceptibility to ventricular arrhythmias. Therefore it was felt that pacing the heart by means of electrodes placed on the surface of the heart were required to make measurement of electrical alternans a useful predictive physiologic measure.

In addition the prior art for processing the recorded physiologic waveforms is limited, particularly in regard to its ability to assess subtle beat-to-beat variability in waveforms in the presence of intercycle interval variability, or abnormal heart-beats—such as premature atrial and ventricular beats, and to assess the statistical significance of a measured level of a temporal pattern of waveform variability such as alternans. The prior art for processing physiologic waveforms must be improved in order to make analysis of cycle-to-cycle variability in physiologic waveforms a practical clinical means of assessing physiologic stability in patients. Such improvements may be particularly necessary for preferred embodiments of the present invention that use means other than endocardial pacing for adjustment of heart rate, that may result in additional incidence of abnormal beats, or intercycle interval variability (the heart-beat interval variability is minimal during endocardial pacing), and introduce extrinsic noise which may complicate the interpretation of the statistical significance of a measured level of a temporal pattern of waveform variability.

It is an object of the present invention to provide a novel less-invasive method and apparatus for achieving the desired heart rate disclosed for the first time herein for the purpose of assessing physiologic stability from analysis of cycle-to-cycle variability in physiologic waveforms. It is further the object of the present invention to provide novel improvements in the processing of physiologic waveforms to permit the accurate assessment cycle-to cycle variability in physiologic waveforms under clinical conditions.

SUMMARY OF THE INVENTION

A preferred embodiment of the present invention utilizes physiologic stress to adjust the heart rate to the desired range for the purposes of analyzing cycle-to-cycle variability in physiologic waveforms. Such physiologic stress may include exercise, administration of pharmacologic agents which alter heart rate (such as atropine, isoproterenol, and dobutamine), pacing the heart through an esophageal electrode, or application of lower body negative pressure. Such physiologic stresses are greatly preferable to endocardial pacing as a means to adjusting heart rate because they are less-invasive, pose less risk to the patient, and are less costly. Furthermore many patients that would most benefit from assessment of their risk of heart rhythm disturbances, routinely undergo physiologic stress tests in order to assess the partial occlusion of coronary vessels by atherosclerosis. The type of analysis performed during such stress tests is entirely different than that of the references cited above for the analysis of cycle-to-cycle variability in physiologic waveforms for the assessment of physiologic stability. For example, during a standard stress test for the detection of coronary artery disease, the physician attempts to visually identify certain gross constant changes which may appear in the electrocardiographic waveforms as a result of the stress if a partially occluded coronary vessel is present. Alternatively, the physician may attempt to measure stress induced changes in the pattern of uptake of an administered radioisotopic compound into the heart tissue using a suitable detection camera. In the method of the current invention the assessment of a patient's risk of ventricular arrhythmias can be performed at the same time as the patient is undergoing physiologic stress for other purposes. Thus, for example, the patient may undergo stress testing to assess the presence of coronary artery disease and to assess his risk for the presence of coronary artery disease. This is of great advantage to the patient, to the physician, and is cost effective. While physiologic stress is used to alter the physiologic state of subjects for the purposes of detecting coronary artery disease and other purposes, it has not been previously used to adjust heart rate to a desired range for the purpose of eliciting a particular temporal pattern of subtle beat-to-beat variability in physiologic waveform morphology such as alternans in the electrocardiogram. Previously it was not realized that measurements of electrical alternans made in the absence of the heart being paced by electrodes placed on the surface of the heart, could provide information predictive of a patient's myocardial electrical stability. In particular, direct pacing of the heart was thought to be required to achieve a heart rate and to eliminate beat-to-beat variability in intercycle interval which can interfere with the development of electrical alternans. A preferred embodiment of this invention involves the combination of physiologic stress with the measurement of a temporal pattern of subtle cycle-to-cycle variability in physiologic waveform morphology, to provide a practical means of assessing an individual's risk of serious heart rhythm disturbances.

In one preferred embodiment of the current invention the heart rate is adjusted to the desired range disclosed herein by one or more of various types of physiologic stress including exercise, pharmacologic stress, pacing the heart by means of an esophageal catheter, or lower body negative pressure. These are all much less risky and invasive methods than endocardial pacing. Preferred embodiments include method and apparatus for adjusting the heart rate to the desired level, means for monitoring the heart rate, and means for minimizing the noise generated by the physiologic stress that may interfere with the assessment of cycle-to-cycle variability in the physiologic waveforms being analyzed. Preferred embodiments also include improvements in the analysis algorithm to enhance the assessment of cycle-to-cycle variability in physiologic waveforms by permitting real-time analysis of waveform variability, reduction in the effect of intercycle variability on waveform variability, improved means for determining the statistical significance of the level of alternans, handling of abnormal beats such as atrial and ventricular premature beats, and assessment of the statistical significance of a measured level of a temporal pattern of variability in waveform morphology.

DESCRIPTION OF THE PREFERRED EMBODIMENT

Figure 1:
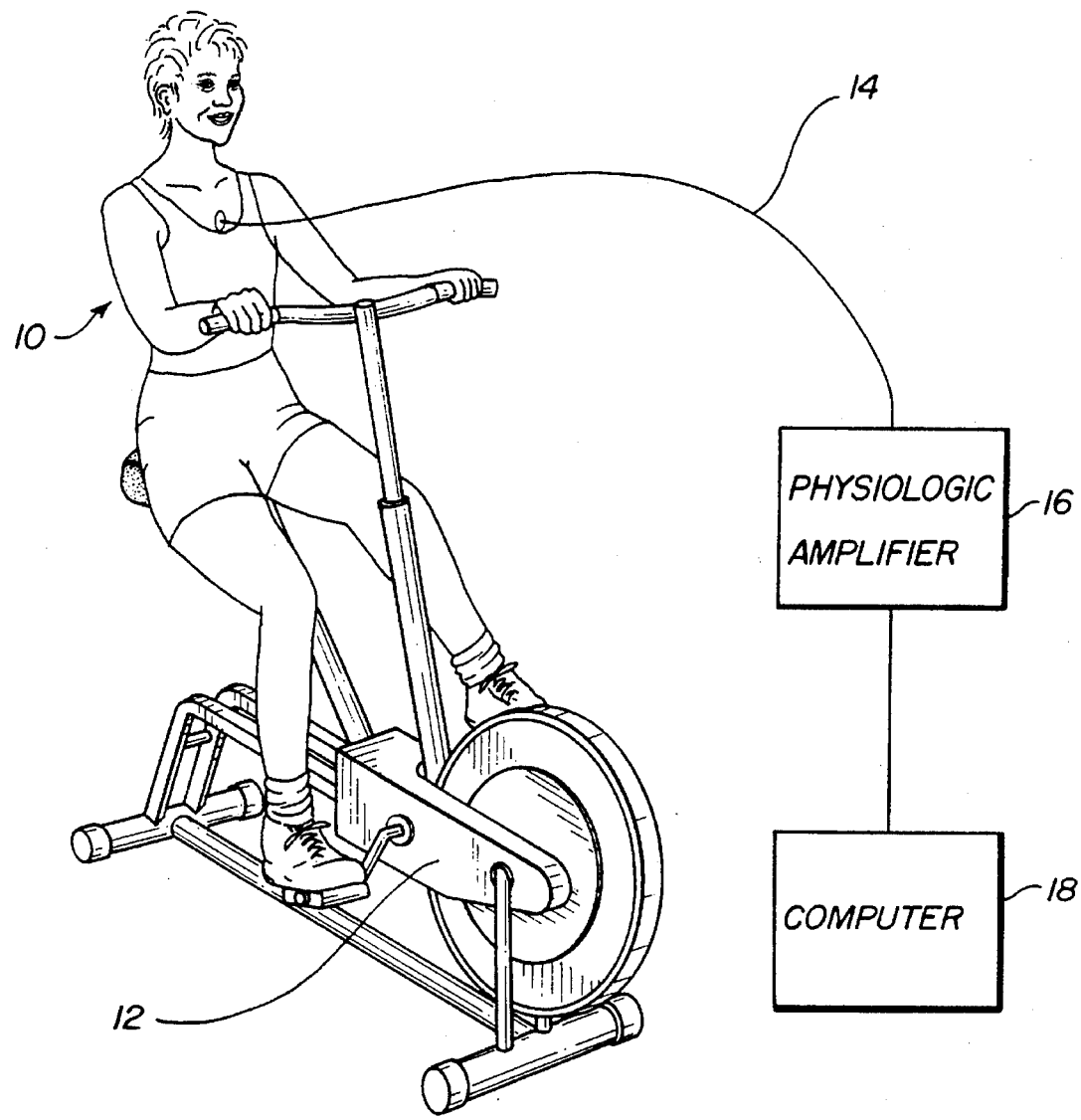
FIG. 1 is a schematic block diagram illustrating an apparatus used to obtain physiologic waveforms during the physiologic stress of exercise.
Figure 2:
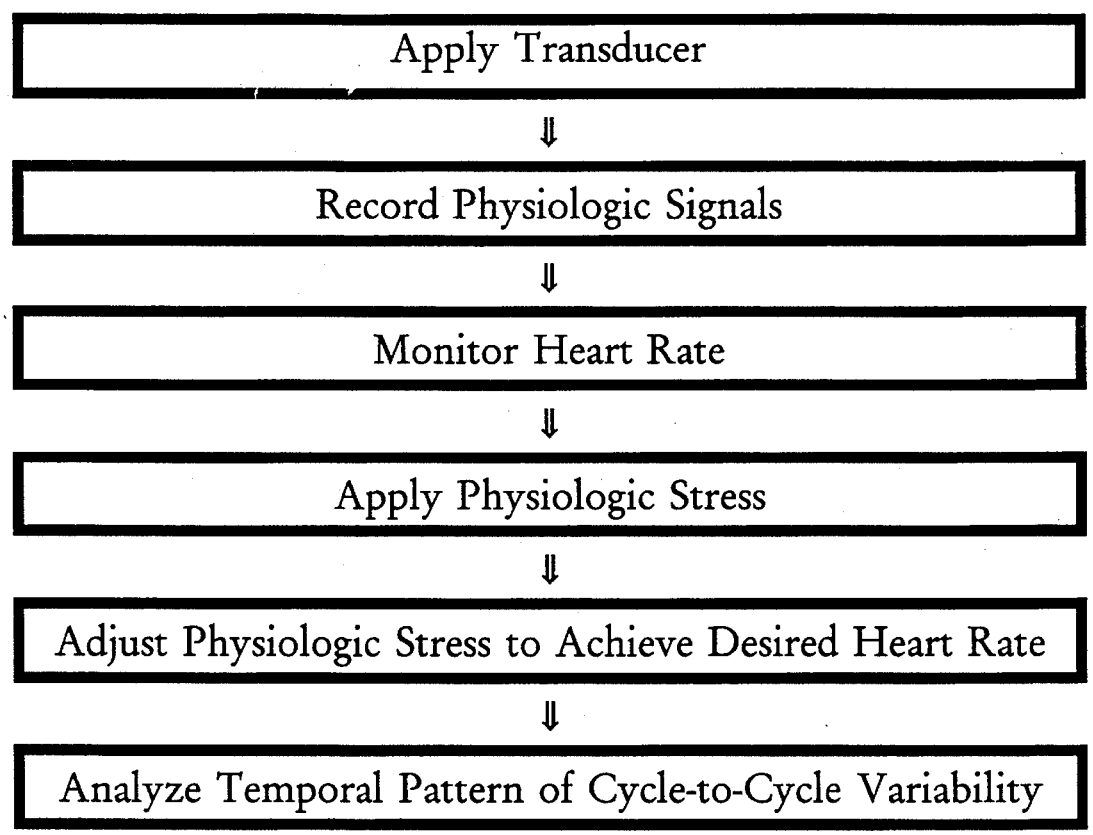
FIG. 2 is a flow chart of the steps of the method of the invention.

In a preferred embodiment of this invention, one or more transducers are applied to a subject and physiologic signals are determined. Means for continual measurement of heart rate are applied. Such means may involve measurement of heart rate from the electrocardiogram using techniques well known in the art. The physiologic state of the subject is altered by subjecting the subject to a physiologic stress other than pacing the heart with electrodes directly applied to a surface of the heart, and the heart rate of the subject is adjusted to the desired range. The physiologic signals are then analyzed, preferably using a digital computer, to obtain a measure of the temporal pattern of cycle-to-cycle variability in the physiologic waveforms such as electrical alternans.

With reference to the single figure of the drawing, which illustrates a preferred embodiment of the invention, a subject 10 is shown on a bicycle 12. The subject 10 has transducers (not shown) applied to an appropriate portion of the body, such as the chest. The transducers communicate through a cable 14 to a physiologic amplifier 16 and then to a computer 18, for analysis of detected signals.

Adjustment of Heart Rate

Physiologic waveform variability may depend greatly on the repetition rate of the waveform. In the case of the electrocardiographic waveform, the development of alternans is rate dependent. The level of alternans is fairly constant over the heart rate range of approximately 100 to 150 beats per minute which is optimal for measuring the electrical alternans pattern of electrocardiographic waveform variability. In the clinical study cited above (Smith et. al., 1988) the heart rate was maintained in this range by pacing the heart by means of an endocardial catheter whose tip lies within the heart. However, placement of an endocardial catheter is an invasive procedure; it is desirable to adjust heart rate to the desired range without the use of an endocardial catheter. In the method of this invention the heart rate is adjusted to the desired range by any of several means not requiring the placement of an endocardial catheter. These means include:

i) adjusting the heart rate by having the subject exercise, for example, on an upright bicycle, on a supine bicycle or on a treadmill. Such method would include a means of measuring heart rate and using such measurement to adjust the level of exercise so that the heart rate is maintained within a desired range. In one preferred embodiment of this invention, the apparatus of this invention is combined with the apparatus used to conduct exercise stress tests to detect the presence of coronary artery disease. This latter apparatus usually includes a treadmill or bicycle or other equipment for performing controlled exercise and equipment for recording electrocardiographic signals. This combination of apparatus is desirable furthermore because many patients in whom one would want to assess physiologic waveform variability, one would also wish to perform an exercise stress test to detect the presence of coronary artery disease.

The level of exercise may be altered to adjust the subject's heart rate in a variety of ways. For example, when a subject is exercising on a bicycle the resistance of the bicycle to pedaling may be altered and/or the subject may be instructed to alter the pedaling speed. For example, when a treadmill is being used the speed of the treadmill may be altered or the incline of the treadmill may be altered.

One problem in the use of exercise as a physiologic stress in the adjustment of heart rate is the fact that exercise introduces motion noise that may interfere with the analysis of cycle-to-cycle variability in physiologic waveform variability. In a preferred embodiment of this invention the exercise parameters are adjusted in such a way to both set the heart rate in the desired range and to minimize the effect of such noise. For example during bicycle exercise it is found that the recorded electrocardiograms contains motion artifact at frequencies corresponding to the pedal rate and its harmonics. The electrical alternans signal occurs at a fundamental frequency equal to half the heart rate and odd harmonics of the fundamental frequency. It is thus desirable to set the pedal rate so that frequency content of the pedaling signal and the frequency content of the alternans signal overlap as little as possible, consistent with achieving a target heart rate and comfortable pedal rates. For example, if one wishes to minimize the overlap between the pedaling signal fundamental and second harmonic and the alternans fundamental and third harmonic, and the pedal rate and its second harmonic both lie between half the heart rate and three halves of the heart rate, then the pedal rate should be set at two-thirds of the heart rate (obtained by solving the equation $PR-HR/2=3\ HR/2-2\ PR$, where HR is the heart rate and PR is the pedal rate). Furthermore, in the method reported by Smith et. al. (1988, cited above) a reference frequency band was used to estimate the noise in the alternans measurement. It thus would also be useful to minimize the overlap between the frequency content of the pedaling signal and the reference noise band. This noise band corresponds to the frequency band of 0.43 HR to 0.46 HR in the power spectrum computed in Smith et. al. (1988) reference. After taking into account the aliasing about the Nyquist frequency of HR/2 occurring in the computation of that spectrum, this noise band corresponds to the unaliased frequency bands of (0.43 HR+nHR to 0.46 HR+nHR, and 0.54 HR+nHR to 0.57 HR+nHR where n is the set of non-negative integers). So if PR and 2 PR lie between the upper edge of the noise band at 0.57 HR and the lower edge of the noise band located at 1.43 HR, then 0.57 HR<PR<0.715 HR with PR optimally being set at 0.6425 HR. If PR lies between 0.57 HR and 1.43 HR but 2 PR lies between the band edges of 1.57 HR and 2.43 HR this implies 0.785 HR<PR<1.215 HR with PR optimally being equal to the HR. If PR is less than the band edge at 0.43 HR and 2 PR lies above the band edge at 0.57 HR this implies that PR lies between 0.285 HR and 0.43 HR with an optimal frequency of 0.3575 HR.

Using such considerations protocols may be established defining target pedaling rates for target heart rates, eg:

| Target Heart Rate (beats per minute) | Target Pedal Rate (revolutions per minute) |
| --- | --- |
| 105–115 | 65–75 |
| 100–110 | 63–72 |
| 105–115 | 33–45 |
| 100–110 | 31–43 |

The operator may choose a protocol appropriate for the subject, the subject is instructed to maintain the pedal rate in the desired range (the apparatus displays to the subject the actual pedaling rate and the target range), and the resistance to pedaling is adjusted automatically by the apparatus or manually by the operator to maintain the heart rate within the desired range. The analysis algorithm may ignore data collected which does not fall within the specified limits of heart rate and pedal rate if the apparatus has means to measure pedal rate as well as heart rate. Means of measuring pedal rate may include an electronic interface with a revolution rate meter on the bicycle, or an accelerometer on the patient's leg, or means to analyze the electrocardiogram signal noise.

Alternatively, data may be collected during a standard bicycle exercise stress test used for other purposes such as the detection of coronary artery disease, and the analysis algorithm only analyze the data which falls within the specified limits of heart rate and pedal rate if the apparatus has means to measure pedal rate as well as heart rate.

Similar considerations apply to the conduct of a treadmill stress test, except that the during a treadmill test motion artifact is introduced into the electrocardiogram at a fundamental frequency of half the step rate and the harmonics of the fundamental. So the desired step rate ranges may be calculated by setting SR=2 PR where SR is the step rate on the treadmill and PR is the pedal rate calculated above for bicycle exercise. The operator may select a protocol with designated heart rate and step rate ranges. The apparatus may indicate to the subject his actual step rate and target range, using a means of measuring step rate such as an accelerometer or means to analyze the electrocardiogram signal noise. The operator may set the speed of the treadmill to make achieving the desired step rate comfortable to the subject, and then the incline of the treadmill may be adjusted manually by the operator or automatically by the apparatus so that the heart rate is maintained within the desired range. The analysis algorithm may ignore data segments in which the target heart rates and pedal rates do not fall within the desired ranges. Alternatively, the data may collected during a standard treadmill stress test conducted for other purposes such as the detection of coronary artery disease, and only data segments analyzed are those in which the step and target heart rates fall within the target ranges; and/or ii) adjusting the heart rate by administration of pharmacological agents which alter heart rate. Examples of drugs which might be used to increase heart rate include parasympathetic blocking agents, such as atropine and glycopyrrulate, beta-sympathetic agonists such as isoproterenol, dopamine and dobutamine, and vasodilators such as nitroprusside. In each case the method of the invention would involve measuring heart rate and adjusting the dosage of the drug to maintain heart rate in the desired range. Alternatively, the data could be collected during a standard pharmacologic stress test conducted for the purpose of detecting coronary artery disease, and only the data segments analyzed are those in which the target heart falls within the desired range; and/or iii) electrically pacing the heart at the desired rate by means of a catheter placed through the nose or mouth into the esophagus and/or into the stomach; and/or iv) adjusting of heart rate by means of applying lower body negative pressure (here negative pressure is taken to mean negative with respect to ambient atmospheric pressure). in the method of this aspect of the invention the lower extremities are placed in a negative pressure chamber, the heart rate is measured, and the level of negative pressure is adjusted to maintain heart rate in the desired range.

Real-Time Computation of Physiologic Waveform Variability

In one preferred embodiment of this invention, measures of alternans or other measures of the temporal pattern of waveform variability are computed in real-time as the data is accumulated. This is accomplished by computing statistical measures of the waveform variability which are updated as each new waveform is obtained, rather than waiting until the entire set of waveforms are recorded ant then computing the statistical measures. This allows the operator to determine while the data is being accumulated whether sufficient data has been accumulated to make a determination of whether a certain feature of waveform variability, such as alternans, is present, its magnitude and level of statistical confidence of the measure. Thus the operator can determine in real-time whether sufficient data has been accumulated and the measurement can be stopped or whether data collection needs to be continued or whether the data is of deficient quality and the collection technique needs to be modified (e.g. one of the ECG electrodes is too noisy and needs to be replaced). None of the references cited above teach the computation of alternans or other measures of waveform variability in real-time. While Nearing et. al. (1991, cited above) and Nearing and Verrier (1993, cited above) teach how to analyze variation in the level of alternans during a previously recorded data epoch, they do not teach real-time analysis of alternans while the data is being collected. In fact in Nearing and Verrier (1993, cited above, pp2607) the authors specifically state that even the raw unprocessed signals could not be viewed in real-time, "The Streamer software does not allow data to be viewed on the screen while being stored . . . "

Handling of Abnormal Beats

Grossly abnormal waveforms such as premature atrial and ventricular beats disrupt subtle temporal pattern of beat-of-beat variability in waveform morphology. In a preferred embodiment of this invention abnormal beats are identified by determining if their morphology differs from the normal waveform morphology by more than a predetermined threshold or if the preceding intercycle interval differs from the mean intercycle interval by more than some predetermined threshold. The statistical properties of the variability in waveform morphology is determined only in the data segments between abnormal beats. In one preferred embodiment alternans is measured by determining a measure of the difference in shape between even and odd waveforms. This method of measuring alternans can be applied to multiple short data segments unlike spectral analysis and Fourier analysis methods which require continuous data records. In a preferred embodiment these methods for handling of abnormal beats are applied to data collected during physiologic stress.

Improved Means for Determining the Statistical Significance of the Level of Alternans Smith and Cohen (U.S. Pat. No. 4,802,491 cited above) report a method for analyzing the temporal pattern of variability in physiologic waveforms. In this method a physiological signal is digitized and waveforms are identified using methods well known in the field. The waveforms are aligned, for example using cross-correlation methods, and a reference fiducial point is identified for each waveform. Each waveform may be labeled by an index i and sample points within a waveform are labeled by an index j representing the offset, jt, from the fiducial point. Here t is the sampling interval. When multiple electrocardiographic signals are recorded simultaneously in the same subject, each lead may be similarly sampled, and sample points referenced. The sampled waveforms are analyzed to determine the level of alternans within a segment of the physiologic waveform. A power spectrum method is used to obtain three parameters: the energy of the alternating component, the noise energy, and the standard deviation of the noise energy. In the prior art, these measures were combined to obtain an index of the level of alternans (e.g. the square-root of (the energy of the alternating component minus the energy of the noise)) or an index of the statistical significance of the alternans (the ratio of energy of the alternating component minus the energy of the noise)/(standard deviation of the energy of the noise). Such indices suffer from the defect that they do not enable one to determine with statistical confidence whether the level of alternans exceeds some upper threshold or conversely whether the level of alternans is less than some lower threshold. This may be of importance if for example it is demonstrated that an subjects whose level of alternans exceeds an upper threshold have a high risk of ventricular arrhythmias and patients whose level of alternans is less than some lower threshold have a low risk of alternans. In this embodiment of the invention indices are created which enable one to determine with a specified level of statistical certainty whether the alternans level exceeds an upper threshold or is less than some lower threshold (the upper and lower thresholds need not necessarily be different). The outcome of the alternans determination is thus positive (alternans level with statistical confidence exceeds upper threshold), negative (alternans level with statistical confidence is less than lower threshold), or indeterminate (neither positive or negative). For example, a test that alternans with statistical confidence exceeds an upper threshold level is whether the energy of the alternating component minus the energy of the noise exceeds the upper threshold by a multiple of the standard deviation of the energy of the noise. An example of a test that alternans with statistical confidence is less than a lower threshold is whether the energy of the alternating component minus the energy of the noise is less than the lower threshold by a multiple of the standard deviation of the energy of the noise. In each case the multiple of the standard deviation of the energy of the noise used determines the level of statistical confidence. Values of the multiple between 1 and 5 are conveniently used.

In another embodiment of this invention, the level of alternans (for example the energy of the alternating component minus the energy of the noise) and the uncertainty of the alternans level (for example the standard deviation of the noise) are computed for a measurement made in a certain subject. Then an empirical previously determined relationship between the level of alternans and probability of disease (e.g. risk of arrhythmias) is used (said relationship may incorporate the presence of known risk factors in the subject such as history of myocardial infarction and low ejection fraction). Probability of disease in this subject is then determined by integrating the probability distribution of the alternans level (defined in terms of the alternans level and uncertainty) over the empirical relationship between alternans level and risk of disease.

While the above discussion for determining the level and statistical significance is presented in terms of alternans, it is understood that the method of this invention can be similarly applied to any measure of physiologic waveform variability.

One advantage over the prior art of these improved methods for determining the statistical significance of the level of alternans is that if they are determined during, or shortly following, the data collection process one may determine whether the amount of data collected is sufficient to make a statistically confident prediction of disease risk in an individual or whether additional or less noisy data need to be collected. If sufficient data has been collected to make a determination, the data collection process may be stopped.

Compensation for the Effects of Intercycle Interval Variability

Intercycle interval variability may disrupt the subtle cycle to cycle variability in the morphology of the physiologic waveform. In a preferred embodiment the effect of intercycle variability on variation on waveform morphology is reduced by creating a filter which relates variation in intercycle intervals to changes in waveform morphology and using this filter to adjust the waveforms to compensate for the effect of intercycle interval variation. In one preferred embodiment the filter is a multidimensional linear finite impulse moving average filter (relating the amplitude of the waveform at each offset from a fiducial point in the waveform to the sequence of preceding intercycle intervals. In a preferred embodiment these methods for compensating for the effects of intercycle variability are applied during physiologic stress.

What is claimed is:

1. Method for assessing a temporal pattern of cycle-to-cycle variability in physiologic waveforms of a subject comprising:

applying one or more transducers to the subject;

recording one or more physiologic signals containing the physiologic waveforms;

monitoring the subject's heart rate;

applying a physiologic stress to the subject other than pacing the heart via electrodes applied directly to the surface of the heart;

adjusting the physiologic stress to achieve a heart rate within a desired range; and analyzing the temporal pattern of cycle-to-cycle variability in the physiologic waveforms.

2. The method of claim 1 wherein the step of applying one or more transducers to a subject comprises applying body surface electrodes to a surface and wherein the step of recording physiologic signals comprises recording electrocardiograms.

3. The method of claim 2 wherein the step of analyzing the temporal pattern of cycle-to-cycle variability in the physiologic waveforms comprises measuring the alternans pattern of the variation of the physiologic waveforms.

4. The method of claim 1 wherein the step of analyzing the temporal pattern of cycle-to-cycle variability in the physiologic waveforms comprises measuring the alternans pattern of variation of the physiologic waveforms.

5. The method of claim 1 wherein the step of applying a physiologic stress to the subject comprises having the subject exercise.

6. The method of claim 5 wherein the step of applying a physiologic stress to the subject comprises the subject pedalling a bicycle.

7. The method of claim 5 in which the exercise comprises walking on a treadmill.

8. The method of claim 1 in which the physiologic stress applied is the administration of a pharmacologic agent that alters heart rate.

9. The method of claim 1 in which the physiologic stress involves electrically pacing the heart by means of a catheter placed through the nose or mouth into the esophagus and/or into the stomach.

10. The method of claim 1 in which the physiologic stress applied is the application of lower body negative pressure.

11. The method of claim 1 wherein the step of analyzing the temporal pattern of cycle-to-cycle variability in the physiologic waveforms is conducted while the physiologic signals are being recorded.

12. A system for assessing a temporal pattern of cycle-to-cycle variability in physiologic waveforms comprising:

means for applying one or more transducers to a subject to detect physiologic signals;

means for recording said physiologic signals from the subject;

means for monitoring the subject's heart rate;

means for applying a physiologic stress to the subject other than pacing the heart via electrodes applied directly to the surface of the heart;

means for adjusting the physiologic stress to achieve a heart rate within a desired range; and means for analyzing a temporal pattern of cycle-to-cycle variability in the physiologic signals.

13. The system of claim 12 where said one or more transducers are body surface electrodes and the recorded signals are electrocardiograms.

14. The system of claim 13 wherein the means for analyzing the temporal pattern of cycle-to-cycle variability in the physiologic waveform comprises means for detecting an alternans pattern of waveform variation.

15. The system of claim 12 wherein the means for analyzing the temporal pattern of cycle-to-cycle variability in the physiologic signals comprises means for detecting an alternans pattern of waveform variation.

16. The system of claim 12 wherein the means for applying a physiologic stress to the subject comprises means for enabling the subject to exercise.

17. The system of claim 16 wherein the means for allowing the subject to exercise comprises a bicycle.

18. The system of claim 16 in which the exercise comprises walking on a treadmill.

19. The apparatus of claim 12 in which the physiologic stress applied is the administration of a pharmacologic agent that alters heart rate.

20. The apparatus of claim 12 in which the physiologic stress involves electrically pacing the heart by means of a catheter placed through the nose or mouth into the esophagus and/or into the stomach.

21. The system of claim 12 in which the physiologic stress applied is the application of lower body negative pressure.

22. The system of claim 12 wherein the means for analyzing the temporal pattern of cycle-to-cycle variability in the physiologic waveforms comprises means for conducting the analysis while the physiologic signals are being recorded.

23. Method for assessing a temporal pattern of cycle-to-cycle variability in a physiologic waveform comprising:

physiologically stressing a subject to achieve a heart rate within a desired range other than by pacing the heart via electrodes applied directly to the surface of the heart;

detecting physiologic waveform signals from the subject; and analyzing the temporal pattern of cycle-to-cycle variability in the physiologic waveform signals.

24. The method of claim 23 wherein the analyzing step comprises detecting alternans.

25. The method of claims 23 or 24 wherein the analyzing step comprises performing quantitative analysis of the physiologic waveform signals.

26. The method of claim 25 wherein the physiologic stress is exercise.

27. The method of claims 23 or 24 wherein the physiologic stress is exercise.

28. The method of claim 27 wherein the exercise includes a rhythmic component.

29. The method of claim 28 wherein the rhythmic component is selected to minimize the interference with the physiologic waveform signals.

30. The method of claim 29 wherein the rhythmic component frequency is selected to avoid interference with the alternans frequency.

31. The method of claims 29 or 30 wherein the exercise is turning a crank.

32. The method of claim 31 further including adjusting resistance to turning the crank to achieve the heart rate within the desired range.

33. The method of claim 31 wherein the turning rate is approximately one-third heart rate.

34. The method of claim 31 wherein the turning rate is approximately two-thirds heart rate.

35. The method of claim 31 wherein the crank is a bicycle pedal.

36. The method of claim 28 wherein the exercise is walking on a treadmill.

37. The method of claim 36 wherein incline of the treadmill is selected to achieve a heart rate within the desired range.

38. The method of claim 36 wherein step rate of the walking is between 0.285 and 0.43 of the heart rate.

39. Method for assessing the temporal pattern of cycle-to-cycle variability in a physiologic waveform in a subject comprising:

detecting physiologic waveform signals from the subject during a period of physiologic stress other than pacing the heart via electrodes applied directly to the surface of the heart; and analyzing the temporal pattern of cycle-to-cycle variability in the physiologic waveform signals when heart rate of the subject is in a desired range.

40. Method for assessing the temporal pattern of cycle-to-cycle variability in a physiologic waveform in a subject comprising:

detecting physiologic waveform signals from the subject during a period of physiologic stress other than pacing the heart via electrodes applied directly to the surface of the heart having a rhythmic component; and analyzing the temporal pattern of cycle-to-cycle variability in the physiologic waveform signals when the heart rate of the subject is in a desired range and the rhythmic component does not substantially interfere with the physiologic waveform signals.

41. The method of claims 39 or 40 wherein the temporal pattern is alternans.

42. The method of claim 41 wherein the physiologic stress is exercise.

43. The method of claims 39 or 40 wherein the physiologic stress is ordinary activity.

44. The method of claims 39 or 40 wherein the physiologic stress is exercise.

45. The method of claim 44 wherein the exercise is turning a crank.

46. The method of claim 45 wherein the turning rate is one-third heart rate.

47. The method of claim 45 wherein the turning rate is two-third heart rate.

48. The method of claim 45 wherein the crank is a bicycle pedal.

49. The method of claim 48 wherein the bicycle exercise is conducted according to a protocol designed for the detection of the presence of coronary artery disease and data segments.

50. The method of claim 44 wherein the exercise is walking on a treadmill.

51. The method of claim 50 in which treadmill exercise is conducted according to a protocol designed for detection of coronary artery disease.

52. A system for assessing a temporal pattern of cycle-to-cycle variability in a physiologic waveform comprising:

exercise apparatus for use by a subject to achieve a heart rate in a desired range;

transducer apparatus responsive to physiologic waveform signals in the subject during the use of the exercise apparatus to generate electrical signals; and computing apparatus for analyzing the electrical signals to determine the temporal pattern of cycle-to-cycle variability in the physiologic waveform.

53. The system of claim 52 wherein the temporal pattern is alternans.

54. The system of claims 52 or 53 wherein the exercise apparatus is a bicycle.

55. The system of claims 52 or 53 wherein the exercise apparatus is a treadmill.

56. A system for assessing the temporal pattern of cycle-to-cycle variability in a physiologic waveform comprising:

exercise apparatus for use by a subject to alter heart rate;

transducer apparatus responsive to physiologic waveform signals in the subject during the use of the exercise apparatus to generate electrical signals; and computing apparatus for analyzing the electrical signals when heart rate of the subject is in a desired range to determine the temporal pattern of cycle-to-cycle variability in the physiologic waveform.

57. A system for assessing a temporal pattern of cycle-to-cycle variability in a physiologic waveform comprising:

exercise apparatus for use by a subject to alter heart rate;

transducer apparatus responsive to physiologic waveform signals in the subject during the use of the exercise apparatus to generate electrical signals; and computing apparatus for analyzing the electrical signals when heart rate of the subject is in a desired range and use of the exercise apparatus does not substantially interfere with the physiologic waveform signals to determine the temporal pattern of cycle-to-cycle variability.

58. The system of claims 56 or 57 wherein the temporal pattern is alternans.

59. The system of claims 56 or 57 wherein the exercise apparatus is a bicycle.

60. The system of claims 56 or 57 wherein the exercise apparatus is a treadmill.

* * * * *

UNITED STATES PATENT AND TRADEMARK OFFICE
CERTIFICATE OF CORRECTION

PATENT NO. : 5,570,696

DATED : November 5, 1996

INVENTOR(S) : Jeffrey M. Arnold, Paul Albrecht, Kevin S. Librett, Richard J. Cohen It is certified that error appears in the above-indentified patent and that said Letters Patent is hereby corrected as shown below:

Column 7, line 17: after "may" and before "collected," please insert -- be --;

Column 7, line 19: after "and" and before "only", please insert -- the --; and

Column 7, line 59: please delete "ant" and insert therefor -- and --.

Signed and Sealed this

Eighteenth Day of February, 1997

Attest:

BRUCE LEHMAN

Attesting Officer

Commissioner of Patents and Trademarks